(12) United States Patent
Whiston

(10) Patent No.: US 7,442,841 B2
(45) Date of Patent: Oct. 28, 2008

(54) EXTRACTION PROCESS

(75) Inventor: Keith Whiston, Darlington (GB)

(73) Assignee: Invista North America S.A R.L., Wilmington, DE (US)

(*) Notice: Subject to any disclaimer, the term of this patent is extended or adjusted under 35 U.S.C. 154(b) by 0 days.

(21) Appl. No.: 11/839,599

(22) Filed: Aug. 16, 2007

(65) Prior Publication Data

US 2008/0051609 A1 Feb. 28, 2008

Related U.S. Application Data

(60) Provisional application No. 60/901,053, filed on Feb. 12, 2007, provisional application No. 60/838,957, filed on Aug. 18, 2006.

(51) Int. Cl.
*C07C 45/78* (2006.01)
*C07C 29/74* (2006.01)

(52) U.S. Cl. .............. 568/338; 568/343; 568/832; 568/835

(58) Field of Classification Search .......... 568/338, 568/343, 832, 835
See application file for complete search history.

(56) References Cited

U.S. PATENT DOCUMENTS

| 4,283,560 | A | * | 8/1981 | Chao et al. | 568/366 |
| 4,982,018 | A | * | 1/1991 | Gosch et al. | 568/835 |
| 4,990,692 | A | * | 2/1991 | Gosch et al. | 568/835 |
| 5,004,837 | A | * | 4/1991 | Baur et al. | 568/342 |
| 5,298,665 | A | * | 3/1994 | Janssen et al. | 568/342 |
| 5,728,890 | A | * | 3/1998 | Hamamoto et al. | 568/361 |
| 6,677,490 | B2 | * | 1/2004 | Clark et al. | 568/344 |
| 2003/0018223 | A1 | * | 1/2003 | Takamatsu et al. | 568/835 |

* cited by examiner

*Primary Examiner*—Sikarl A Witherspoon

(57) ABSTRACT

A process for the separation of
- an alcohol from a non-polar solvent;
- a ketone from a non-polar solvent;
- an alcohol from a mixture of a ketone and a non-polar solvent; or
- a mixture of an alcohol and a ketone from a non-polar solvent;

said process comprising contacting at least one ionic liquid with a mixture comprising a non-polar solvent and at least one of an alcohol and a ketone.

31 Claims, No Drawings

EXTRACTION PROCESS

CROSS-REFERENCE TO RELATED APPLICATIONS

This application claims benefit of priority from Provisional Application No. 60/838,957 filed Aug. 18, 2006 and Provisional Application No. 60/901,053 filed Feb. 12, 2007. This application hereby incorporates by reference Provisional Application No. 60/901,053 in its entirety.

FIELD OF THE INVENTION

The present invention relates to the separation of alcohols and ketones in a mixture with a non-polar solvent, such as an alkane, using an ionic liquid. The invention particularly relates to the separation of cycloalkanols, cycloalkanones and cycloalkanes.

BACKGROUND

The oxidation of cyclohexane and subsequent separation of a mixture of cyclohexanone and cyclohexanol from unreacted cyclohexane is a key step in the manufacture of both adipic acid and caprolactam. The primary industrial use of caprolactam is as a monomer in the production of nylon-6. Adipic acid is a monomer used in the production of nylon-6,6 amongst other applications.

Conventionally, the oxidation of cyclohexane is carried out at a relatively low conversion of less than 10%. The primary oxidation products of cyclohexane are cyclohexane hydroperoxide, cyclohexanol and cyclohexanone. In a typical commercial cyclohexane oxidation process cyclohexyl hydroperoxide is then decomposed to cyclohexanol and cyclohexanone, either in the reactor or in a separate unit operation. This process as a whole can be described for the purposes of the present invention as the cyclohexane oxidation process. The desired final oxidation product after decomposition of cyclohexyl hydroperoxide is a mixture of primarily cyclohexanone and cyclohexanol. The mixture must then be separated from the unreacted cyclohexane whereby the unreacted cyclohexane can then typically be recycled to the oxidation reaction. This

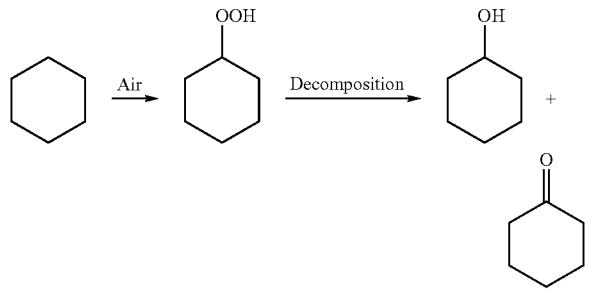

separation is commercially carried out by distillation, and since the great majority of the cyclohexane is recycled, it is this process step which accounts for a high proportion of process steam usage.

Therefore, there is a need for alternative separation technology that can reduce steam usage and, as a consequence, reduce the substantial energy cost associated with separation through distillation.

In addition, the process for manufacturing caprolactam requires cyclohexanone as a starting material that is substantially free of cyclohexanol. Currently, this level of purity is achieved commercially through distillation, which again is an energy intensive process.

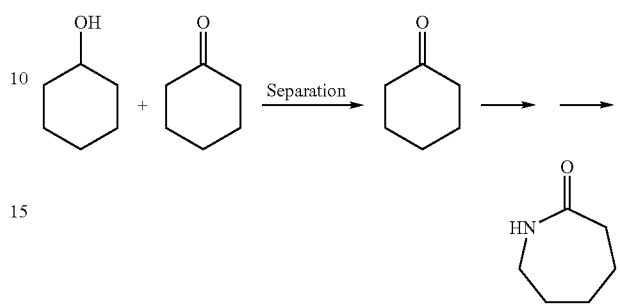

Liquid-liquid or solvent separation (also known as liquid-liquid or solvent extraction) processes are well known in the art as processes for the separation of components of a mixture. Liquid-liquid separation is based on the transfer of component(s) from one liquid phase into another liquid phase and is used to separate component(s) selectively from a mixture. Mixing two immiscible liquids leads to a phase separation, and the formation of two liquid layers, also known as phases or fractions. The less dense liquid will form the upper layer, and the more dense liquid will form the lower layer. Liquid-liquid separation relies on the different relative solubilities of a component in two immiscible liquids. In particular, if the soluble component is allowed to mix freely with two immiscible liquids, it will partition between the two liquid phases thus formed such that the component will generally be dissolved in one of the liquid phases to a greater extent than in the other liquid phase. Generally, liquid-liquid separation utilises a water-based, or aqueous, phase and an organic phase (comprising an organic solvent) that is substantially immiscible in water. In this instance, when the aqueous phase and the organic phase are mixed with, for example, an aqueous solution of two separable components, if one of the separable components is more soluble in the organic phase it will be separated and become dissolved in the organic phase. Assuming that the other separable component is more soluble in the aqueous phase, then the two separable components will have been separated. Liquid-liquid separation can be a powerful technique provided suitable liquids are used. The traditional aqueous phase/organic phase separation would not be possible for the separation of a cycloalkanol and a cycloalkanone from a cycloalkane because all three of these components would dissolve more readily in the organic phase.

Liquid-liquid extraction technology can also be carried out using two organic phases which are substantially immiscible with each other and in one of which the solubility of the component to be extracted is much greater than the other. A disadvantage of liquid-liquid extraction technology is that final recovery of the components extracted from the initial mixture can be complicated by the volatility of the extracting solvent. Typically final recovery of the components of interest is carried out by distillation, but often the extracting solvent is of comparable volatility to the desired product. Therefore, recovery of the component of interest can be very difficult, and process may also be energy intensive in terms of steam requirements. It is a feature of the present invention that such limitations are avoided by the use of Ionic Liquid(s) as the extracting solvent. Because Ionic Liquids are substantially non-volatile, they do not interfere with the recovery of the component of interest during final recovery. Recovery of said component may, therefore, be effected by simple flash recovery without the need for complicated separation technology with a corresponding reduction in energy (e.g., steam) requirements.

For the manufacture of caprolactam from the oxidation of cyclohexane, it is further necessary to separate cyclohexanol from cyclohexanone, either directly from a mixture of the two or in the presence of cyclohexane. This is because caprolactam manufacture requires only cyclohexanone as a starting material. Conventionally, this separation is carried out by distillation wherein the separation of cyclohexanone from cyclohexanol requires significant energy and a high capital investment in the distillation column required. Liquid-liquid extraction technology is not conventionally used for the separation of cyclohexanone and cyclohexanol since, for this application, it is a requirement of the extraction solvent that it selectively removes one component only from the mixture. Conventional solvents which are suitable for use in a solvent extraction process will not selectively extract cyclohexanol from cyclohexanone.

In liquid-liquid separation, a distribution coefficient for a given separable component can be quoted as a measure of the extent to which a separable component is separated. In traditional liquid-liquid separation, the distribution coefficient is equal to the concentration of the separable component in the organic-based phase divided by the concentration of the separable component in the aqueous phase. The distribution coefficient can be a function of a number of different parameters e.g. temperature.

SUMMARY OF THE INVENTION

The object of the present invention is to provide an improved method for the separation of an alcohol from a ketone in a mixture of these compounds in a non-polar solvent, and for the separation of an alcohol and/or a ketone from a non-polar solvent. It is a particular object of this invention to provide an improved method for the separation of a cycloalkanol from a cycloalkanone in a mixture of these compounds in a non-polar solvent (such as a cycloalkane), and for the separation of a cycloalkanol and/or a cycloalkanone from a non-polar solvent (such as a cycloalkane).

DETAILED DESCRIPTION OF THE INVENTION

According to the present invention, there is provided a process for the separation of
an alcohol from a non-polar solvent;
a ketone from a non-polar solvent;
an alcohol from a mixture of a ketone and a non-polar solvent; or
a mixture of an alcohol and a ketone from a non-polar solvent;

said process comprising contacting at least one ionic liquid with a mixture comprising a non-polar solvent and at least one of an alcohol and a ketone.

As used herein, the term "alcohol" encompasses acyclic and cyclic aliphatic alcohols, and in one embodiment refers to an (alkyl-OH) group, and in an alternative embodiment to a (cycloalkyl-OH) group, i.e. a "cycloalkanol".

As used herein, the term "ketone" encompasses acyclic and cyclic aliphatic ketones, and in one embodiment refers to an (alkyl-(C=O)-alkyl) group and in an alternative embodiment to a cyclic compound corresponding to a cycloalkane wherein a ($CH_2$) group is replaced with a (C=O) group, i.e. a "cycloalkanone".

As used herein, the term "alkane" refers to (alkyl-H) and the term "cycloalkane" refers to (cycloalkyl-H).

As used herein, the term "alkyl" refers to a straight-chain or branched-chain saturated monovalent hydrocarbon radical, and particularly one having from 1 to 20 carbon atoms. By way of non-limiting example, suitable alkyl groups include methyl, ethyl, propyl, butyl, pentyl, hexyl, octyl, nonyl, dodecyl and eicosyl. Said alkyl groups may be substituted by one or more halogen atoms, the same or different, but are preferably unsubstituted.

As used herein, the term "cycloalkyl" refers to a cyclic saturated monovalent hydrocarbon radical, having 3-20 carbon atoms. By way of non-limiting example, suitable cycloalkyl groups include cyclopropyl, cyclobutyl, cyclopentyl, cyclohexyl, cycloheptyl, cyclooctyl, cyclononyl and cyclododecyl. Preferably, the cycloalkyl groups contain from 5 to 12 carbon atoms. Said cycloalkyl groups may be substituted by one or more halogen atoms, the same or different, but are preferably unsubstituted.

As used herein, the term "non-polar solvent" refers to a compound which is immiscible with an ionic liquid. In one embodiment, the term "non-polar solvent" refers to a solvent which has a dielectric constant of no more than 5, preferably no more than 3.0, more preferably no more than 2.5, measured at 20° C. and atmospheric pressure according to ASTM D924-92. In a preferred embodiment, the term "non-polar solvent" refers to cyclic and acyclic aliphatic hydrocarbons, and particularly cyclic and acyclic saturated aliphatic hydrocarbons, i.e. alkanes and cycloalkanes, such as pentanes, hexanes, heptanes, octanes and cyclohexane etc. Said non-polar aliphatic hydrocarbons may be substituted by one or more halogen atoms, the same or different, but are preferably unsubstituted.

Thus, in one embodiment of the present invention, there is provided a process for the separation of:
a cycloalkanol from a non-polar solvent;
a cycloalkanone from a non-polar solvent;
a cycloalkanol from a mixture of a cycloalkanone and a non-polar solvent; or
a mixture of a cycloalkanol and a cycloalkanone from a non-polar solvent;

said process comprising contacting at least one ionic liquid with a mixture comprising a non-polar solvent and at least one of a cycloalkanol and a cycloalkanone.

In a further embodiment of the present invention, there is provided a process for the separation of
an alcohol from an alkane;
a ketone from an alkane;
an alcohol from a mixture of a ketone and an alkane; or
a mixture of an alcohol and a ketone from an alkane;

particularly wherein said alcohol and said ketone are acyclic, said process comprising contacting at least one ionic liquid with a mixture comprising an alkane and at least one of an alcohol and a ketone.

In this embodiment, said alcohol contains a number of carbon atoms which may be different to, but is preferably the same as, the number of carbon atoms in the ketone and/or alkane present in the mixture to be separated, and said ketone has a number of carbon atoms which may be different to, but is preferably the same as, the number of carbon atoms in the alcohol and/or the alkane present in the mixture to be separated.

In a particularly preferred embodiment of the present invention, there is provided a process for the separation of
- a cycloalkanol from a cycloalkane;
- a cycloalkanone from a cycloalkane;
- a cycloalkanol from a mixture of a cycloalkanone and a cycloalkane; or
- a mixture of a cycloalkanol and a cycloalkanone from a cycloalkane;

said process comprising contacting at least one ionic liquid with a mixture comprising a cycloalkane and at least one of a cycloalkanol and a cycloalkanone.

In this embodiment, said cycloalkanol contains a number of carbon atoms which may be different to, but is preferably the same as, the number of carbon atoms in the cycloalkanone and/or cycloalkane present in the mixture to be separated, and said cycloalkanone has a number of carbon atoms which may be different to, but is preferably the same as, the number of carbon atoms in the cycloalkanol and/or the cycloalkane present in the mixture to be separated.

Thus, the invention encompasses:
(i) processes for the separation of an alcohol and/or a ketone from the corresponding aliphatic hydrocarbon, i.e. the alkane or cycloalkane having the corresponding number of carbon atoms, and for the separation of said alcohol from said corresponding ketone and aliphatic hydrocarbon;
(ii) processes for the separation of an alcohol and/or a ketone from an aliphatic hydrocarbon (e.g. an alkane or cycloalkane) which has a different number of carbon atoms, and for the separation of said alcohol from said ketone and aliphatic hydrocarbon; and
(iii) processes for the separation of an alcohol and/or a ketone from a non-polar solvent as defined herein, and for the separation of said alcohol from said corresponding ketone and non-polar solvent.

Moreover, in the processes described under (ii) and (iii) above, said alcohol and said ketone may themselves have different numbers of carbon atoms to each other, but typically they will have the same number of carbon atoms.

According to the present invention there is further provided a method for the use of at least one ionic liquid for the separation of an alcohol and/or ketone from a non-polar solvent, or for the separation of an alcohol from a ketone in a mixture of these compounds in a non-polar solvent, particularly when said alcohol is a cycloalkanol and said ketone is a cycloalkanone, and particularly when said alcohol is a cycloalkanol and said ketone is a cycloalkanone and said non-polar solvent is a cycloalkane.

In one embodiment, the cycloalkyl groups contain 6 carbon atoms, in which case the separation process described herein is particularly concerned with the separation of a cyclohexanol and/or a cyclohexanone from a cyclohexane, and with the separation of a cyclohexanol from a cyclohexanone and a cyclohexane.

In another embodiment, the cycloalkyl groups contain 12 carbon atoms, in which case the separation process described herein is particularly concerned with the separation of a cyclododecanol and/or a cyclododecanone from a cyclododecane, and with the separation of a cyclododecanol from a cyclododecanone and a cyclododecane.

Thus, the mixture to be separated can therefore comprise, for instance, a cycloalkanol and a cycloalkane; or a cycloalkanone and a cycloalkane; or a cycloalkanol and a cycloalkanone and a cycloalkane.

The process of the present invention involves a liquid-liquid separation wherein one of the liquid phases is an ionic liquid-based phase and the other is a non-polar solvent phase, such as an organic hydrocarbon-based phase, that is substantially immiscible in the ionic liquid-based phase. As used herein, the term "substantially immiscible" is intended to mean immiscible to the extent that two separate phases are formed. The process of the present invention thus relies upon the different relative solubility/solubilities of the component/components to be separated, i.e. the separable component(s), in the ionic liquid-based phase and the non-polar solvent phase. In particular, a separable component will partition itself between the ionic liquid-based phase and the non-polar solvent phase in such a way that more of the or each separable component will be dissolved in the ionic liquid-based phase.

Once brought into contact, the ionic liquid(s) and the mixture comprising an alcohol and/or a ketone in a non-polar solvent (e.g. a cycloalkanol and/or a cycloalkanone in a cycloalkane) is referred to herein as the "separation mixture". As used herein, the term "contacting" is intended to mean the bringing together of the ionic liquid(s) with said mixture comprising an alcohol and/or a ketone in a non-polar solvent to form the separation mixture. The ionic liquid(s) and said mixture comprising an alcohol and/or a ketone in a non-polar solvent can be contacted in a container (i.e., reaction vessel) that is suitable for said contact.

Typically, the separation mixture is shaken, mixed or stirred vigorously for a period of time, hereinafter referred to as the contacting time, to allow thorough dispersion of the ionic liquid(s) throughout said mixture comprising an alcohol and/or a ketone in a non-polar solvent. It will be appreciated that if the contacting time is too short, the ionic liquid(s) will not be fully dispersed throughout said mixture comprising an alcohol and/or a ketone in a non-polar solvent, and separation of the separable component(s) will be inefficient, i.e. only a small proportion of the separable component(s) present in the separation mixture will be separated. Increasing the contacting time of the separation mixture will increase the dispersion of the ionic liquid(s) and said mixture comprising an alcohol and/or a ketone in a non-polar solvent, and the efficiency of the separation will be increased, i.e. a larger proportion of the separable component(s) in the separation mixture will be separated. This increase of separation efficiency with contacting time will occur until a maximum possible proportion of the total volume of separable component(s) has been separated for the separation conditions used (e.g. type of ionic liquid, temperature etc) i.e. maximum separation has been obtained. At this point, contacting the separation mixture for any longer would not provide any benefit to the separation of the separable component(s). Therefore, as used herein, the contacting time is preferably greater than 30 seconds, more preferably greater than 60 seconds and typically not greater than 5 minutes, although longer times periods may be used with satisfactory results.

Subsequent to the vigorous shaking, mixing or stirring, the separation mixture is allowed to settle for another period of time, hereinafter referred to as the "settling time". During the settling time the separation mixture will separate into an ionic-liquid based phase and a non-polar solvent-based phase. The settling time should be long enough to allow the ionic liquid-based phase and the non-polar solvent-based phase to fully separate, at which point the system is described as being in equilibrium. The settling time is preferably longer than 1 minute, more preferably longer than 2 minutes and typically no longer than 10 minutes, although longer times periods may be used with satisfactory results.

The mixture comprising an alcohol and/or a ketone in a non-polar solvent, and particularly at least one of a cycloalkanol and a cycloalkanone in a cycloalkane, may be formed by an oxidation step preceding the separation process. For instance, in the case of the oxidation of a cycloalkane such as cyclohexane as described hereinabove, the oxidation step may be, but is not limited to, oxidation with air alone or in the presence of a cobalt or other transition metal catalyst followed by decomposition of the resulting cyclohexyl hydroperoxide, either thermally or through other catalytic means. For the purposes of this invention, an oxidation step followed by a cyclohexyl hydroperoxide decomposition step followed by a separation, or contacting, step is defined as one oxidation and separation cycle. A plurality of oxidation and separation cycles can be carried out. In this instance, a cycloalkane-based phase or fraction resulting from the separation may be recycled for further oxidation.

In addition, following the separation step, the ionic liquid-based phase can be physically separated from the non-polar solvent-based phase. This physical separation can be carried out using any suitable apparatus Furthermore, the separable component(s), e.g. a cycloalkanol and/or a cycloalkanone, can be removed from the ionic liquid-based phase and said ionic liquid(s) can be recycled and re-used, for example, in a further separation step.

Commercial equipment for liquid-liquid extraction contacting and separation may be generally classified into two categories: stage-wise and continuous (differential) contacting. Stage-wise operations typically involve a mixing step followed by a phase separation, or settling, step in devices generally known as mixer-settlers. Operations can be carried out in sequential batch fashion, in which case it is common for the same vessel to serve alternating functions of mixing and settling. Operations can also be carried out with continuous flow, for which the mixing and settling steps are usually, but not always performed in separate vessels. In continuous flow systems the necessary mixing time and settling time are obtained by proper sizing of equipment volume or holdup. Examples of commercial mixing equipment known to those skilled in the art includes in-line static mixers, jet mixers, injectors, orifices or mixing nozzles, valves, centrifugal pumps, agitated line mixers, packed tubes, mechanically agitated vessels, gas or vapor agitated vessels, and vessels with circulating flow loops. Examples of commercial settling equipment known to those skilled in the art includes gravity settlers, decanters, centrifugal cyclones, centrifuges, and settler auxiliaries such as coalescers, separating membranes, and electrical field devices (for electrically conducting emulsions or dispersions). Any type of mixer and settler can be combined to produce a stage. Stages can be arranged in a multi-stage cascade to achieve additional separation efficiency. Multi-stage arrangements can employ a variety of liquid flow schemes such as counter-current flow, co-current flow, cross-current flow, staged-flow, and so forth. Compact equipment consisting of alternative mixing and settling elements can be constructed.

Continuous (differential) contacting equipment is usually arranged for multi-stage counter-current contact of insoluble liquids without repeated complete separation of the liquids from each other between stages. However it may also be arranged co-current or cross current. The liquids remain in continuous contact with each other throughout the equipment. Counter-current flow is maintained by differences in densities of the liquids in conjunction with gravity or centrifugal force. Commercial equipment known to those skilled in the art includes gravity-operated extractors such as spray towers, packed towers, or sieve tray towers; gravity-operated extractors with mechanical agitation such as towers with rotating stirrers, rotary-disk contactors, Mixco (Oldshue-Rushton) multiple-mixer columns, Scheibel columns, Kuhni contactor columns, liquid pulsed towers, and reciprocating plate columns; and centrifugal extractors.

The separation process of the present invention may form one or more separation steps in the manufacture of adipic acid or caprolactam. The separation steps of these processes have traditionally been performed by distillation.

In embodiment (a) the separable component is a cycloalkanone which is separated from a cycloalkane. The ionic liquid(s) is contacted with a mixture of the cycloalkanone and the cycloalkane. In this embodiment, the ionic liquid(s) and the mixture of the cycloalkanone and the cycloalkane is known as separation mixture (a). The process of this embodiment involves a liquid-liquid separation wherein one of the liquid phases is an ionic liquid-based phase and the other is a cycloalkane-based phase that is substantially immiscible in the ionic liquid-based phase. In this embodiment, the distribution coefficient of the cycloalkanone between the ionic liquid-based phase and the cycloalkane-based phase is greater than 1.5 and preferably greater than 3.

In embodiment (b), the separable component is a cycloalkanol which is separated from a cycloalkane. The ionic liquid(s) is contacted with a mixture of the cycloalkanol and the cycloalkane. In this embodiment, the ionic liquid(s) and the mixture of the cycloalkanol and the cycloalkane is known as separation mixture (b). The process of this embodiment involves a liquid-liquid separation wherein one of the liquid phases is an ionic liquid-based phase and the other is a cycloalkane-based phase that is substantially immiscible in the ionic liquid-based phase. In this embodiment, the distribution coefficient of the cycloalkanol between the ionic liquid-based phase and the cycloalkane-based phase is greater than 1.5 and preferably greater than 3.

In embodiment (c) the separable component is a cycloalkanol which is separated from a mixture of a cycloalkanone and a cycloalkane. The ionic liquid(s) is contacted with a mixture of the cycloalkanol, the cycloalkanone and the cycloalkane. In this embodiment, the ionic liquid(s) and the mixture of the cycloalkanol, the cycloalkanone and the cycloalkane is known as separation mixture (c). The process of this embodiment involves a liquid-liquid separation wherein one of the liquid phases is an ionic liquid-based phase, and the other liquid phase is a cycloalkane-based phase that is substantially immiscible in the ionic liquid-based phase. The separation of a cycloalkanol from a cycloalkanone and a cycloalkane according to the process in this embodiment can be achieved when the distribution coefficient for the cycloalkanol between the ionic liquid-based phase and the cycloalkane-based phase is greater than 1, and the distribution coefficient for the cycloalkanone between the ionic liquid-based phase and the cycloalkane-based phase is less than 1. This embodiment has application to the separation of cyclohexanol from cyclohexanone for caprolactam manufacture. In this embodiment, the distribution coefficient of the cycloalkanol between the ionic liquid-based phase and the cycloalkane-based is greater than 1.5 and preferably greater than 3.

In embodiment (d) the separable components are a mixture of a cycloalkanone and a cycloalkanol which are separated from a cycloalkane. The ionic liquid(s) is contacted with a mixture of the cycloalkanol, the cycloalkanone and the cycloalkane. In this embodiment, the ionic liquid(s) and the mixture of the cycloalkanol, the cycloalkanone and the cycloalkane is known as separation mixture (d). The process of this embodiment involves a liquid-liquid separation wherein one of the liquid phases is an ionic liquid-based phase and the other is a cycloalkane-based phase that is substantially immiscible in the ionic liquid-based phase. In this embodiment, the distribution coefficient of the cycloalkanol and the cycloalkanone between the ionic liquid-based phase and the cycloalkane-based phase is greater than 1.5 and preferably greater than 3.

In each of embodiments (a) to (d), the mixtures to be separated may also contain materials other than the cycloalkanol, cycloalkanone and cycloalkane components. Depending on the distribution coefficient of these other materials between the ionic liquid-based phase and the cycloalkane-based phase, these other materials will either remain in the cycloalkane-based phase or be separated into the ionic liquid-based phase along with the separable component. In particular, cyclohexylhydroperoxide (CHHP) may be present in the separation mixture of cyclohexanol, cyclohexanone and cyclohexane. In these circumstances, CHHP would be separated with the cyclohexanol and/or cyclohexanone into the ionic liquid-based phase.

It will be appreciated that the processes of embodiments (a) to (d) are also applicable to the generic cases in which the above references to a cycloalkanol, a cycloalkanone and a cyclohexane are respectively replaced with references to an alcohol, a ketone and a non-polar solvent.

The ionic liquid(s) of the present invention may consist of a single ionic liquid or a mixture of two or more ionic liquids, i.e. a mixture of 2, 3, 4, 5, 6 etc different ionic liquids. Typically, one or two, and typically only one ionic liquid is used.

Preferably the ionic liquid(s) comprises a cation selected from one or more of 1-alkylpyridinium, alkyl- or poly-alkylpyridinium, phosphonium ($PR_4^+$), alkyl- or polyalkylphosphonium, imidazolium, alkyl- or polyalkylimidazolium, ammonium ($NR_4^+$), alkyl- or polyalkylammonium, alkyl- or polyalkylpyrazolium, alkyl- or polyalkylpyrrolidinium, alkyl or polyalkylazepinium, alkyloxonium or alkysulfonium.

Each R group of the phosphonium and ammonium cations may be separately selected from the group of substituents consisting of hydrogen, hydroxyl, alkyl, alkyl ethers, alkyl esters, alkyl amides, alkyl carboxylic acids, or sulfonate.

More preferably the ionic liquid(s) comprises a cation selected from one or more of 1-alkylpyridinium, alkyl- or poly-alkylpyridinium, imidazolium, alkyl- or polyalkylimidazolium.

When a mixture of two or more ionic liquids is used, the cations of each of the ionic liquids present in the mixture may be the same or different.

Preferably the anion of the ionic liquid(s) is selected from one or more of a halide, preferably chloride, bromide or iodide, a nitrate, an alkylsulfate or alkyl polyalkoxysulfate, such as methanesulfonate, trifluoromethanesulfonate and hydrogensulfonate, anions based on nitrogen, phosphorous, boron, silicon, selenium, tellurium, halogens, and oxoanions of metals. Suitable anions include, but are not limited to bis(trifluoromethylsulfonyl)amide ($NTf_2^-$), tetrafluoroborate ($BF_4^-$), trifluoromethylsulfonyl ($Tf^-$), methoxyethylsulfonate, 2-methoxyethylsulfonate, ethoxyethylsulfonate, 2-ethoxyethylsulfonate, (methoxypropoxy)propylsulfonate, 1-(1-methoxypropoxy)-propylsulfonate, (methoxyethoxy)-ethylsulfonate, 1-(1-methoxyethoxy)-ethylsulfonate, methyl(diethoxy)ethylsulfonate, 1-methyl(diethoxy)ethylsulfonate, carboxylate, formate, acetate, dicyanimide and trifluoromethanesulfonate.

More preferably the anion of the ionic liquid(s) is selected from one or more of an alkylsulfate or alkyl polyalkoxysulfate, bis(trifluoromethylsulfonyl)amide ($NTf_2^-$) and tetrafluoroborate ($BF_4^-$).

When a mixture of two or more ionic liquids is used, the anion of each of the ionic liquids present in the mixture may be the same or different.

Preferably the ionic liquid(s) will comprise at least one $C_2$-$C_6$ alkyl group. The $C_2$-$C_6$ alkyl group may be a substituent on either the anion or the cation of the ionic liquid(s). More preferably the $C_2$-$C_6$ alkyl group is a substituent on the cation of the ionic liquid(s). When the ionic liquid(s) consists of a single ionic liquid, the single ionic liquid present preferably contains at least one $C_2$-$C_6$ alkyl group substituent. When the ionic liquid(s) consists of two or more ionic liquids, preferably at least one of the ionic liquids present contains at least one $C_2$-$C_6$ alkyl group substituent, more preferably two or more of the ionic liquids present contain at least one $C_2$-$C_6$ alkyl group substituent, i.e. 2, 3, 4, 5 etc of the ionic liquids present contain at least one $C_2$-$C_6$ alkyl group substituent. Most preferably, all the ionic liquids present in the at least on ionic liquid contain at least one $C_2$-$C_6$ alkyl group substituent.

The ionic liquid(s) of the present invention is preferably selected from the group consisting of N-ethylpyridinium bis(trifluoromethanesulfonyl)amide;
N-Methyl-N'-butylimidazolium tetrafluoroborate;
N-Methyl-N'-butylimidazolium bis(trifluoromethanesulfonyl)amide;
trimethyl-(2-hydroxyethyl)ammonium bis(trifluoromethanesulfonyl)amide;
N-Methyl-N'-ethylimidazolium 2-methoxyethylsulfonate;
N-butyl-N-methylpyrrolidinium bis(trifluoromethanesulfonyl)amide;
N-Methyl-N'-butylimidazolium 2-methoxyethylsulfonate;
N-Methyl-N'-butylimidazolium bromide;
N-Methyl-N'-butylimidazolium 2-ethoxyethylsulfonate;
N-Methyl-N'-butylimidazolium 1-(1-methoxypropoxy)-propylsulfonate;
N-Methyl-N'-butylimidazolium 1-(1-methoxyethoxy)-ethylsulfonate;
N-Methyl-N'-butylimidazolium 1-methyl(diethoxy)ethylsulfonate; or
N-Methyl-N-(butyl-4-sulfonic acid)pyrrolidinium trifluoromethanesulfonate or mixtures thereof.

Most preferably the ionic liquid(s) is N-butyl-N-methylpyrrolidinium bis(trifluoromethanesulfonyl)amide or N-Methyl-N'-butylimidazolium 1-(1-methoxypropoxy)-propylsulfonate.

Ionic liquids most suitable for the separation of an alcohol from a non-polar solvent, particularly when said alcohol is a cycloalkanol (and particularly a cyclohexanol) and said non-polar solvent is a cycloalkane (particularly a cyclohexane) are:
N-ethylpyridinium bis(trifluoromethanesulfonyl)amide;
N-Methyl-N'-butylimidazolium tetrafluoroborate;
N-Methyl-N'-butylimidazolium bis(trifluoromethanesulfonyl)amide;
trimethyl-(2-hydroxyethyl)ammonium bis(trifluoromethanesulfonyl)amide;
N-Methyl-N'-ethylimidazolium 2-methoxyethylsulfonate;
N-butyl-N-methylpyrrolidinium bis(trifluoromethanesulfonyl)amide;
N-Methyl-N'-butylimidazolium 2-methoxyethylsulfonate;
N-Methyl-N'-butylimidazolium bromide;
N-Methyl-N'-butylimidazolium 2-ethoxyethylsulfonate;
N-Methyl-N'-butylimidazolium 1-(1-methoxypropoxy)-propylsulfonate;
N-Methyl-N'-butylimidazolium 1-(1-methoxyethoxy)-ethylsulfonate;
N-Methyl-N'-butylimidazolium 1-methyl(diethoxy)ethylsulfonate; or
N-Methyl-N-(butyl-4-sulfonic acid)pyrrolidinium trifluoromethanesulfonate, or mixtures thereof.

Ionic liquids most suitable for the separation of an alcohol from a mixture of a non-polar solvent and a ketone, particularly wherein said alcohol is a cycloalkanol (particularly a cyclohexanol) and said ketone is a cycloalkanone (particularly a cyclohexanone) and said non-polar solvent is a cycloalkane (particularly a cyclohexane) are:

N-Methyl-N'-butylimidazolium bromide;
N-Methyl-N'-butylimidazolium 1-(1-methoxyethoxy)-ethylsulfonate;
or N-Methyl-N'-butylimidazolium 2-ethoxyethylsulfonate, or mixtures thereof.

Ionic liquids most suitable for the separation of a ketone from a non-polar solvent, particularly wherein said ketone is a cycloalkanone (particularly a cyclohexanone) and said non-polar solvent is a cycloalkane (particularly a cyclohexane) are:
N-ethylpyridinium bis(trifluoromethanesulfonyl)amide;
N-Methyl-N'-butylimidazolium tetrafluoroborate;
N-Methyl-N'-butylimidazolium bis(trifluoromethanesulfonyl)amide;
trimethyl-(2-hydroxyethyl)ammonium bis(trifluoromethanesulfonyl)amide;
N-Methyl-N'-ethylimidazolium 2-methoxyethylsulfonate;
N-butyl-N-methylpyrrolidinium bis(trifluoromethanesulfonyl)amide;
N-Methyl-N'-butylimidazolium 2-methoxyethylsulfonate;
N-Methyl-N'-butylimidazolium 1-(1-methoxypropoxy)-propylsulfonate;
N-Methyl-N'-butylimidazolium 1-methyl(diethoxy)ethylsulfonate; or
N-Methyl-N-(butyl-4-sulfonic acid)pyrrolidinium trifluoromethanesulfonate, or mixtures thereof.

Ionic liquids most suitable for the separation of a mixture of an alcohol and a ketone from a non-polar solvent, particularly when said alcohol is a cycloalkanol (and particularly cyclohexanol) and said ketone is a cycloalkanone (particularly cyclohexanone) and said non-polar solvent is a cycloalkane (particularly a cyclohexane) are:
N-ethylpyridinium bis(trifluoromethanesulfonyl)amide;
N-Methyl-N'-butylimidazolium tetrafluoroborate;
N-Methyl-N'-butylimidazolium bis(trifluoromethanesulfonyl)amide;
trimethyl-(2-hydroxyethyl)ammonium bis(trifluoromethanesulfonyl)amide;
N-Methyl-N'-ethylimidazolium 2-methoxyethylsulfonate;
N-butyl-N-methylpyrrolidinium bis(trifluoromethanesulfonyl)amide;
N-Methyl-N'-butylimidazolium 2-methoxyethylsulfonate;
N-Methyl-N'-butylimidazolium 1-(1-methoxypropoxy)-propylsulfonate;
N-Methyl-N'-butylimidazolium 1-methyl(diethoxy)ethylsulfonate; or
N-Methyl-N-(butyl-4-sulfonic acid)pyrrolidinium trifluoromethanesulfonate or mixtures thereof.

As used herein, the term "ionic liquid" refers to an ionic compound which is liquid below 100° C.

As used herein, the term "distribution coefficient" referring to the liquid-liquid separation refers to the concentration of the separable component in the ionic liquid-based phase divided by the concentration of the separable component in the non-polar solvent-based phase. These concentrations are measured subsequent to settling, i.e. when the separation mixture has reached equilibrium subsequent to the vigorous shaking.

The invention is further illustrated by the following examples. It will be appreciated that the examples are for illustrative purposes only and are not intended to limit the invention as described above. Modification of detail may be made without departing from the scope of the invention.

EXAMPLES (i) Cyclohexanol/Cyclohexanone/Cyclohexane

The present invention is exemplified through separation of cyclohexanol and cyclohexanone from cyclohexane using a general method followed by calculation of the resulting distribution coefficient. To simplify these examples, equal volumes of cyclohexane and ionic liquid have been used. However, it should be noted that in practice the volume of ionic liquid used would preferably be a small fraction of the volume of cyclohexane. It should also be noted that since the distribution coefficient is independent of volume, the data obtained for equivolume experiments will be relevant to industrial application in which the volumes of ionic liquid and cyclohexane may not be equivalent. The general method used for all the examples was as follows.

Stock solution; 250 mg cyclohexanol (Molecular Weight=100 gmol$^{-1}$) and 250 mg cyclohexanone (Molecular Weight=98 gmol$^{-1}$) in 10 g of cyclohexane (Molecular Weight=84 gmol$^{-1}$).

Method: add 1 mL (0.8 g) of stock solution (20 mg each of cyclohexanol and cyclohexanone) to 1 mL of ionic liquid and shake vigorously. After settling time and complete phase separation, 3 drops of the top layer were added to a vial and filled with ethylene chloride. Gas chromatography analysis was used to provide the number of moles of the separable component in each liquid phase. The distribution coefficient for the separation was then calculated.

In addition, Hnmr (Hydrogen Nuclear Magnetic Resonance) was carried out on each layer. In all cases the cyclohexane- or cyclohexanone layer contained less than 5 mole % of ionic liquid, in most cases the amount of ionic liquid in the cyclohexane-based layer was undetectable.

Table 1 details the results of the specific examples with comparisons to water and DMSO (dimethyl sulfoxide), where D is the distribution coefficient.

TABLE 1

| Example | Extracting Solvent | Cyclohexanol | | Cyclohexanone | |
| | | D | Log D | D | Log D |
| --- | --- | --- | --- | --- | --- |
| 1 | H$_2$O | 0.86 | −0.07 | 0.34 | −0.47 |
| 2 | 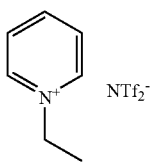 | 1.60 | 0.20 | 3.40 | 0.53 |

TABLE 1-continued
| Example | Extracting Solvent | Cyclohexanol D | Cyclohexanol Log D | Cyclohexanone D | Cyclohexanone Log D |
|---|---|---|---|---|---|
| 3 | 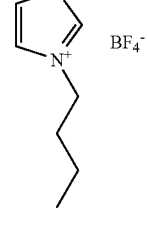 | 1.77 | 0.24 | 2.11 | 0.32 |
| 4 | 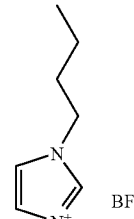 | 2.32 | 0.36 | 1.51 | 0.18 |
| 5 | 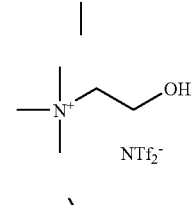 | 2.91 | 0.46 | 3.00 | 0.478 |
| 6 | 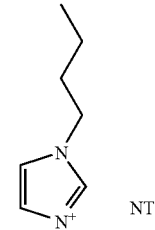 | 4.10 | 0.61 | 4.38 | 0.64 |
| 7 | 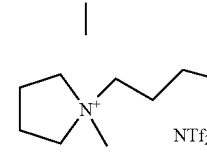 | 5.12 | 0.71 | 5.00 | 0.7 |
| 8 | 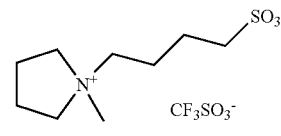 | 5.96 | 0.78 | 0.21 | −0.69 |
| 9 | 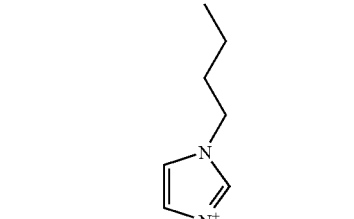 | 6.29 | 0.8 | 1.89 | 0.28 |

TABLE 1-continued

| Example | Extracting Solvent | Cyclohexanol | | Cyclohexanone | |
|---|---|---|---|---|---|
| | | D | Log D | D | Log D |
| | 1-butyl-3-methylimidazolium NTf$_2^-$ | | | | |
| 10 | 1-butyl-3-methylimidazolium Br$^-$ | 6.29 | 0.8 | 0.39 | −0.41 |
| 11 | 1-butyl-3-(2-ethoxyethyl)imidazolium OSO$_3^-$ | 8.02 | 0.90 | 0.92 | −0.04 |
| 12 | 1-butyl-3-(2-(2-methoxyethoxy)ethyl)imidazolium OSO$_3^-$ | 8.19 | 0.91 | 0.24 | −0.62 |

TABLE 1-continued

| | | Cyclohexanol | | Cyclohexanone | |
|---|---|---|---|---|---|
| Example | Extracting Solvent | D | Log D | D | Log D |
| 13 | 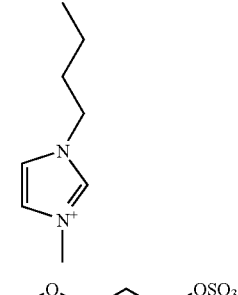 | 18.27 | 1.26 | 1.33 | 0.12 |
| 14 | DMSO | 24.79 | 1.39 | 2.80 | 0.45 |

The difference in the distribution coefficients for cyclohexanol and cyclohexanone in these ionic liquids show the efficiency of separation of cyclohexanol. Thus, these ionic liquids are effective for the separation of cyclohexanol from cyclohexane, and for the separation of cyclohexanol from a mixture of cyclohexanone and cyclohexane.

(ii) Ooctanol/Octanone/Octane

A corresponding set of experiments was conducted to study the extraction of octanol and 2-octanone from octane using ionic liquids. The results are presented in Table 2 below, in which the IL/Octane distribution coefficient is calculated as the concentration of substrate in IL divided by the concentration of substrate in octane.

TABLE 2

| | | IL/Octane | |
|---|---|---|---|
| Ex. | Ionic liquid | Octanol | 2-Octanone |
| 15 | 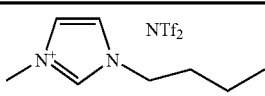 | 1.06 | 2.08 |
| 16 | 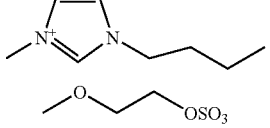 | 2.39 | 0.24 |
| 17 | 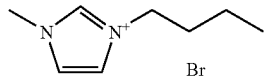 | 1.44 | 0.16 |
| 18 | 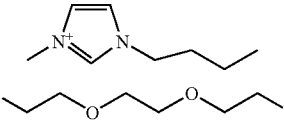 | 6.93 | 0.64 |
| 19 | DMSO | 7.67 | 0.89 |

The difference in the distribution coefficients for octanol and 2-octanone in these ionic liquids demonstrate the separability of octanol and/or 2-octanone from octane (Example 15) and octanol from a mixture of 2-octanone and octane (Examples 16 to 18).

The invention claimed is:

1. A process for the separation of
   an alcohol from a non-polar solvent;
   a ketone from a non-polar solvent;
   an alcohol from a mixture of a ketone and a non-polar solvent; or
   a mixture of an alcohol and a ketone from a non-polar solvent;
   said process comprising contacting at least one ionic liquid with a mixture comprising a non-polar solvent and at least one of an alcohol and a ketone.

2. The process according to claim 1 wherein said alcohol is a cycloalkanol, said ketone is a cycloalkanone, and said non-polar solvent is a cycloalkane.

3. The process according to claim 2 for the separation of a cycloalkanone from a cycloalkane.

4. The process according to claim 2 for the separation of a cycloalkanol from a mixture of cycloalkanone and cycloalkane.

5. The process according to claim 2 for the separation of a mixture of a cycloalkanone and a cycloalkanol from a cycloalkane.

6. The process according to claim 2 for the separation of a cycloalkanol or a cycloalkanone or a mixture thereof from a cycloalkane or the separation of a cycloalkanol from a cycloalkanone and a cycloalkane, wherein on contacting said at least one ionic liquid with the mixture comprising at least one of a cycloalkanol and a cycloalkanone in a cycloalkane, two separate phases are formed wherein the first phase is ionic liquid-based and the second phase is cycloalkane-based.

7. The process according to claim 6 for the separation of a cycloalkanol from a cycloalkanone and a cycloalkane, wherein the two separate phases are allowed to reach equilibrium and wherein at equilibrium the distribution coefficient of the cycloalkanol between the ionic liquid-based phase and the cycloalkane-based phase is greater than 1.5.

8. The process according to claim 7 for the separation of a cycloalkanol from a cycloalkanone and a cycloalkane, wherein said distribution coefficient is greater than 3.

9. The process according to claim 6 for the separation of a cycloalkanol from a cycloalkanone and a cycloalkane, wherein the two separate phases are allowed to reach equilibrium and wherein at equilibrium the distribution coefficient for the cycloalkanol between the ionic liquid-based phase and the cycloalkane-based phase is greater than 1, and the distribution coefficient for the cycloalkanone between the ionic liquid-based phase and the cycloalkane-based phase is less than 1.

10. The process according to claim 6 for the separation of a cycloalkanol from a cycloalkane, wherein the two separate phases are allowed to reach equilibrium and wherein at equilibrium the distribution coefficient of the cycloalkanol between the ionic liquid-based phase and the cycloalkane-based phase is greater than 1.5.

11. The process according to claim 10 for the separation of a cycloalkanol from a cycloalkane, wherein said distribution coefficient is greater than 3.

12. The process according to claim 6 for the separation of a cycloalkanone from a cycloalkane, wherein the two separate phases are allowed to reach equilibrium and wherein at equilibrium the distribution coefficient of the cycloalkanone between the ionic liquid-based phase and the cycloalkane-based phase is greater than 1.5.

13. The process according to claim 12 for the separation of a cycloalkanone from a cycloalkane, wherein said distribution coefficient is greater than 3.

14. The process according to claim 6 for the separation of a mixture of a cycloalkanone and a cycloalkanol from a cycloalkane, wherein the two phase system is allowed to reach equilibrium and wherein at equilibrium the distribution coefficient of the cycloalkanone between the ionic liquid-based phase and the cycloalkane-based phase is greater than 1.5.

15. The process according to claim 14 for the separation of a cycloalkanone and a cycloalkanol from a cycloalkane, wherein said distribution coefficient is greater than 3.

16. The process according to any one of claims 1 to 15, wherein each of said cycloalkanol, cycloalkanone and said cycloalkane contain 3-20 carbon atoms.

17. The process according to any one of claims 1 to 15, wherein the cycloalkanol is cyclohexanol, the cycloalkanone is cyclohexanone and the cycloalkane is cyclohexane.

18. The process according to any one of claims 1 to 15, wherein the cycloalkanol is cyclododecanol, the cycloalkanone is cyclododecanone and the cycloalkane is cyclododecane.

19. The process according to any one of claims 1 to 15, further comprising, prior to said contacting step, the step of oxidation of a cycloalkane followed by a cyclohexyl hydroperoxide decomposition step followed by said contacting step defining one oxidation and separation cycle.

20. The process according to claim 19, comprising a plurality of oxidation and separation cycles, wherein the cycloalkane-based phase or fraction which results from said separation is recycled for oxidation.

21. The process according to claim 20, wherein subsequent to equilibrium being reached, the at least one ionic liquid-based phase is physically separated from the cycloalkane-based phase, and the cycloalkanol and/or cycloalkanone is removed from said at least one ionic liquid and said at least one ionic liquid is recycled.

22. The process according to any one of claims 1 to 15, wherein said at least one ionic liquid consists of a mixture of two or more ionic liquids.

23. The process according to any one of claims 1 to 15, wherein the cation of said at least one ionic liquid is selected from one or more of: 1-alkylpyridinium, alkyl- or poly-alkylpyridinium, phosphonium, alkyl- or polyalkylphosphonium, imidazolium, alkyl- or polyalkylimidazolium, ammonium, alkyl- or polyalkylammonium, alkyl- or polyalkylpyrazolium, alky- or polyalkylpyrrolidinium, alkyl- or polyalkylazepinium, alkyloxonium or alkysulfonium.

24. The process according to any one of claims 1 to 15, wherein the anion of said at least one ionic liquid is selected from one or more of a halide, a nitrate, an alkylsulfate or alkyl polyalkoxysulfate, anions based on nitrogen, phosphorous, boron, silicon, selenium, tellurium, halogens, and oxoanions of metals.

25. The process according to any one of claims 1 to 15, wherein at least one ionic liquid of said at least one ionic liquid comprises at least one $C_2$-$C_6$ alkyl group, wherein the alkyl group may be present on the anion or the cation of said at least one ionic liquid.

26. The process according to any one of claims 1 to 15, wherein said at least one ionic liquid is:
N-ethylpyridinium bis(trifluoromethanesulfonyl)amide;
N-Methyl-N'-butylimidazolium tetrafluoroborate;
N-Methyl-N'-butylimidazolium bis(trifluoromethanesulfonyl)amide;
trimethyl-(2-hydroxyethyl)ammonium bis(trifluoromethanesulfonyl)amide;
N-Methyl-N'-ethylimidazolium 2-methoxyethylsulfonate;
N-butyl-N-methylpyrrolidinium bis(trifluoromethanesulfonyl)amide;
N-Methyl-N'-butylimidazolium 2-methoxyethylsulfonate;
N-Methyl-N'-butylimidazolium bromide;
N-Methyl-N'-ethylimidazolium 2-ethoxyethylsulfonate;
N-Methyl-N'-butylimidazolium 1-(1-methoxypropoxy)-propylsulfonate;
N-Methyl-N'-butylimidazolium 1-(1-methoxyethoxy)-ethylsulfonate;
N-Methyl-N'-butylimidazolium 1-methyl(diethoxy)ethylsulfonate; or
N-Methyl-N-(butyl-4-sulfonic acid)pyrrolidinium trifluoromethanesulfonate, or mixtures thereof.

27. The process according to claim 26, wherein said at least one ionic liquid is N-butyl-N-methylpyrrolidinium bis(trifluoromethanesulfonyl)amide.

28. The process according to claim 26, wherein said at least one ionic liquid is N-Methyl-N'-butylimidazolium 1-(1-methoxypropoxy)-propylsulfonate.

29. A method for the use of at least one ionic liquid for the separation of an alcohol and/or ketone from a non-polar solvent, or for the separation of an alcohol from a ketone in a mixture of these compounds in a non-polar solvent by contacting at least one ionic liquid with a mixture comprising a non-polar solvent and at least one of an alcohol and a ketone.

30. The method according to claim 29 wherein said alcohol is a cycloalkanol and said ketone is a cycloalkanone.

31. The method according to claim 29 wherein said alcohol is a cycloalkanol and said ketone is a cycloalkanone and said non-polar solvent is a cycloalkane.

* * * * *